United States Patent
Li et al.

(10) Patent No.: US 10,354,860 B2
(45) Date of Patent: Jul. 16, 2019

(54) METHOD AND PRECURSORS FOR MANUFACTURING 3D DEVICES

(71) Applicant: AIR PRODUCTS AND CHEMICALS, INC., Allentown, PA (US)

(72) Inventors: Jianheng Li, Emmaus, PA (US); Robert Gordon Ridgeway, Quakertown, PA (US); Xinjian Lei, Vista, CA (US); Raymond Nicholas Vrtis, Orefield, PA (US); Bing Han, Lansdale, PA (US); Madhukar Bhaskara Rao, Carlsbad, CA (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 0 days.

(21) Appl. No.: 14/871,233

(22) Filed: Sep. 30, 2015

(65) Prior Publication Data

US 2016/0225616 A1    Aug. 4, 2016

Related U.S. Application Data

(60) Provisional application No. 62/109,381, filed on Jan. 29, 2015, provisional application No. 62/183,985, filed on Jun. 24, 2015.

(51) Int. Cl.
*H01L 21/02* (2006.01)
*C07F 7/02* (2006.01)
(Continued)

(52) U.S. Cl.
CPC ...... *H01L 21/02219* (2013.01); *C01B 21/087* (2013.01); *C07F 7/10* (2013.01);
(Continued)

(58) Field of Classification Search
None
See application file for complete search history.

(56) References Cited

U.S. PATENT DOCUMENTS

| 6,060,400 A | 5/2000 | Oehrlein et al. |
| 6,437,444 B2 | 8/2002 | Andideh |

(Continued)

FOREIGN PATENT DOCUMENTS

| EP | 1887104 | 2/2008 |
| EP | 1928015 A2 | 6/2008 |

(Continued)

OTHER PUBLICATIONS

M. Belyansky, et al, "Methods of producing plasma enhanced chemical vapor deposition silicon nitride thin films with high compressive and tensile stress", J. Vac. Sci. Technol., 2008, 517-521.

(Continued)

*Primary Examiner* — Fernando L Toledo
*Assistant Examiner* — Valerie N Newton
(74) *Attorney, Agent, or Firm* — Rosaleen P. Morris-Oskanian; Joseph D. Rossi; David K. Benson (57) ABSTRACT

Described herein is an apparatus comprising a plurality of silicon-containing layers wherein the silicon-containing layers are selected from a silicon oxide and a silicon nitride layer or film. Also described herein are methods for forming the apparatus to be used, for example, as 3D vertical NAND flash memory stacks. In one particular aspect or the apparatus, the silicon oxide layer comprises slightly compressive stress and good thermal stability. In this or other aspects of the apparatus, the silicon nitride layer comprises slightly tensile stress and less than 300 MPa stress change after up to about 800° C. thermal treatment. In this or other aspects of the apparatus, the silicon nitride layer etches much faster (Continued)

than the silicon oxide layer in hot $H_3PO_4$, showing good etch selectivity.

34 Claims, 5 Drawing Sheets

(51) Int. Cl.
     *C23C 16/34*      (2006.01)
     *C23C 16/40*      (2006.01)
     *C01B 21/087*     (2006.01)
     *C07F 7/10*       (2006.01)
     *H01L 27/11517*   (2017.01)
     *H01L 27/11556*   (2017.01)
     *H01L 27/11563*   (2017.01)
     *H01L 27/11582*   (2017.01)

(52) U.S. Cl.
     CPC .......... *C23C 16/345* (2013.01); *C23C 16/402* (2013.01); *H01L 21/0217* (2013.01); *H01L 21/02164* (2013.01); *H01L 21/02274* (2013.01); *H01L 27/11517* (2013.01); *H01L 27/11556* (2013.01); *H01L 27/11563* (2013.01); *H01L 27/11582* (2013.01)

(56) References Cited

U.S. PATENT DOCUMENTS

| | | | |
|---|---|---|---|
| 8,319,275 | B2 | 11/2012 | Shim et al. |
| 8,344,385 | B2 | 1/2013 | Kim et al. |
| 8,357,430 | B2 | 1/2013 | Dussarrat et al. |
| 8,933,502 | B2 | 1/2015 | Higashitani et al. |
| 9,018,093 | B2 | 4/2015 | Tsuji et al. |
| 2003/0054670 | A1 | 3/2003 | Wang et al. |
| 2005/0255714 | A1 | 11/2005 | Iyer et al. |
| 2007/0031598 | A1 | 2/2007 | Okuyama et al. |
| 2008/0203487 | A1 | 8/2008 | Hohage et al. |
| 2008/0260969 | A1 | 10/2008 | Dussarrat et al. |
| 2011/0151678 | A1 | 6/2011 | Ashtiani et al. |
| 2011/0236600 | A1 | 9/2011 | Fox et al. |
| 2011/0298038 | A1 | 12/2011 | Son et al. |
| 2012/0034451 | A1 | 2/2012 | Seo et al. |
| 2012/0064682 | A1 | 3/2012 | Jang et al. |
| 2013/0129940 | A1* | 5/2013 | Xiao .............. C07F 7/025 427/578 |
| 2013/0157466 | A1 | 6/2013 | Fox et al. |
| 2013/0220410 | A1 | 8/2013 | Haas et al. |
| 2013/0267081 | A1 | 10/2013 | Fox et al. |
| 2014/0213065 | A1 | 7/2014 | Tsuji et al. |
| 2014/0213067 | A1 | 7/2014 | Murakami et al. |
| 2014/0273531 | A1 | 9/2014 | Niskanen et al. |
| 2014/0284808 | A1 | 9/2014 | Hasebe |
| 2015/0021599 | A1* | 1/2015 | Ridgeway .......... C23C 16/345 257/43 |

FOREIGN PATENT DOCUMENTS

| | | | |
|---|---|---|---|
| JP | 06124942 | A | 5/1994 |
| JP | 11061409 | A | 3/1999 |
| JP | 2009500857 | A | 8/2009 |
| JP | 2011508434 | A | 10/2011 |
| JP | 2011243889 | A | 12/2011 |
| KR | 20120132536 | A | 5/2012 |
| KR | 20140087908 | | 7/2014 |
| KR | 20140087908 | A | 9/2014 |
| WO | 2006018441 | | 2/2006 |
| WO | 2013134661 | A1 | 9/2013 |

OTHER PUBLICATIONS

R. Arghavani, et al, "A Reliable and Manufacturable Method to Induce a Stress of >1 GPa on a P-Channel MOSFET in High Volume Manufacturing", IEEE Electron Device Letters, 2006, 114-116.

B.E.E. Kastenmeier, et al, "Highly selective etching of silicon nitride over silicon and silicon dioxide", J. Vac. Sci. Technol., 1999, 3179-3184.

S. Lim, et al, "Micro Unetched Oxide Defects during Buffered Oxide Etchant Process", ECS Transactions, 2013, 127-132.

L. Diao, et al, "Novel Strip Process Strategy for Metal Gate", ECS Transactions, 2012, 369-376.

J. Lee, et al, "3-D Stacked Active Layers and Vertical Gate NAND Flash String with Single-Crystal Si Channel by Adopting Si/SiGe Selective Etch Process", School of EECS and ISRC, Seoul National University, Seoul, Korea.

M. Jeong, et al, "3-D Stacked NAND Flash String with Tube Channel Structure Using Si and SiGe Selective Etch Process", School of Electrical Engineering and Computer Science, Kyungpook National University, Gyeongbuk, Korea.

C. Ryu, et al, "Issues and Challenges of Cleaning for Nano-scale NAND Flash Memory Manufacturing", ECS Transactions, 2007, 11-18.

J. Koo, et al, "Vertical Structure NAND Flash Array Integration with Paired FinFET Multi-bit Scheme for High-density NAND Flash Memory Application", 2008 Symposium on VLSI Technology Digest of Technical Papers, 120-121.

S. Cho, et al, "Highly Scalable Vertical Bandgap-Engineered NAND Flash Memory", School of Electrical Engineering and Computer Science, Seoul National University, Seoul, Korea, 265-266.

I.G. Baek, et al, "Realization of Vertical Resistive Memory (VRRAM) using cost effective 3D Process", Samsung Electronics Co., Ltd., 737-740.

E.A.V. Ebsworth, et al, "The Preparation and Donor Properties of Some Silylamines", J. Chem. Soc., 1958, 2150-2156.

Ebsworth, E. A. V., et al., "The Preparation and Donor Properties of Some Silylamines", J. Chem. Soc., Jan. 1, 1958, pp. 2150-2156.

Scantlin, William M., "Pentaborane(9)-catalyzed condensation of silylamines", Journal of the Chemical Society [D]: Chemical Communications, No. 20, Jan. 1, 1971, p. 1246.

Scantlin, William M., et al., "Borane-catalyzed condensation of trisilazane and N-methyldisilazane", Inorganic Chemistry, vol. 11, No. 12, Dec. 1, 1972, pp. 3082-3084.

\* cited by examiner

METHOD AND PRECURSORS FOR MANUFACTURING 3D DEVICES

CROSS REFERENCE TO RELATED APPLICATIONS

This application claims the priority of U.S. Provisional Application Nos. 62/109,381, filed on Jan. 29, 2015 and 62/183,985, filed on Jun. 24, 2015, both of which are incorporated by reference herein in their entirety.

BACKGROUND OF THE INVENTION

Worldwide data transfer continues to grow at an explosive rate. Three dimensional (3D) flash memory devices, comprising a plurality of layers or multilayer stacks, such as without limitation 24, 32, 48, 96, 128 or greater layers, allow more data transfer in a smaller footprint. Newer 3D memory devices such as vertical-NAND (VNAND) memory devices have at least twice the write speed, greater than 10 times the endurance, and approximately half the power consumption compared to conventional NAND memory devices, comprise a plurality of layers such as, without limitation 24, 32, 48, or 96 layers or greater. To deposit these multilayer stacks, the end user typically employs alternative deposition of silicon oxide and silicon nitride films. For certain applications, the silicon nitride films are sacrificial layers wherein the layers are removed in one or more subsequent processing steps.

Generally, silicon oxide films have a compressive stress ranging from about −300 to about −100 MegaPascals (MPa). To balance out the compressive stress of the silicon oxide layer and avoid structure cracking or collapsing after depositing multiple layers such as 24, 32 48, 96, or 128 layers, the silicon nitride films should have a tensile stress ranging from about +50 to about +300 MPa. For most silicon-containing precursors, raising the stress of the film typically compromises the film quality. In certain applications, such as those for making NAND and 3D VNAND devices which subject the structure to an epitaxial silicon deposition step which is conducted at temperatures greater than 700° C., the silicon nitride film should also have minimal shrinkage and less than 300 MPa stress change.

US Publ. No. 2014/0284808 describes the use of the precursor tetraethoxysilane (TEOS) for silicon oxide deposition and dichlorosilane for nitride deposition using a chemical vapor deposition (CVD) method at 650~750° C. or higher.

US Publ. No. US 2008/0260969 and U.S. Pat. No. 8,357, 430 both describe methods for high quality plasma enhanced chemical vapor deposition (PECVD) of silicon nitride using the precursor trisilylamine (TSA).

US Publ. No. 2014/0213065 or U.S. Pat. No. 9,018,093 describes a method to deposit stacked layers comprising a first layer and a second layer wherein each stacked layer has the same thickness.

US Publ. No. 2014/0213067 describes a method for SiOCN film deposition or SiCN/SiCO stacks by atomic layer deposition.

There have also been intensive studies on stress controls for $SiH_4$ based silicon nitride films. Some of the topics that these studies addressed are the following: higher $NH_3:SiH_4$ ratio, lower plasma power, higher pressure, and higher temperature to affect resultant tensile stress.

Therefore, there is a need in the art for a 3D memory device or apparatus and method for making same comprising at least one silicon oxide layer and at least one silicon nitride layer that provides one or more of the following advantages: the use of a single silicon-containing precursor to deposit both types of layers; the at least one silicon nitride films having a tensile stress ranging from about 50 to about +300 (MPa) to avoid stress accumulation of the overall multilayer stack; good electrical properties meaning that it retains its insulating nature after processing; excellent thermal stability meaning there is minimal film shrinkage and stress change; higher deposition rate than other precursors such as silane under same conditions to improve throughput and film properties; wet etch selectivity so that the sacrificial nitride layer can be easily removed; improved electrical performance; long term stability; and combinations thereof. To simplify the manufacturing process and improve the throughput, it would be advantageous to deposit high quality silicon oxide and silicon nitride films using a single silicon-containing precursor for both layers.

BRIEF SUMMARY OF THE INVENTION

Described herein is an apparatus comprising at least one silicon oxide layer and at least one silicon nitride layer wherein the at least one silicon oxide layer and the at least one silicon nitride layer have certain characteristics. Also described herein are methods for forming the apparatus, a multilayer stack, or plurality of silicon-containing layers comprising at least one silicon oxide layer and at least one silicon nitride layer to be used, for example, as layers within a memory device, such as, without limitation, a 3D VNAND device.

As previously mentioned, the apparatus comprises a multilayer stack which comprises at least one silicon oxide layer or film and at least one silicon nitride layer or film. In certain embodiments, the number of layers can range from 2 to 1,000 layers comprising silicon oxide and silicon nitride. In one particular embodiment, the multilayer stack or apparatus comprises 24, 48, 64, 96, or 128 stacks of alternating silicon oxide and silicon nitride films wherein each stack consists of one layer silicon oxide and one layer of silicon nitride. In this or other embodiments, the apparatus is comprised of at least 50 stacks or greater of alternating silicon oxide and silicon nitride films. In this or other embodiments, the at least one silicon oxide film described herein has one least one or more of the following properties: a density of about 1.9 grams per cubic centimeter ($g/cm^3$ or g/cc) or greater; a hydrogen content of $4\times10^{22}$ atoms/$cm^3$ or less; a stress of −100 MPa or lower, a dielectric constant of 4.5 or lower, a leakage current of $10^{-9}$ $A/cm^2$ or lower at a film breakdown field of 8 MV/cm or higher; and combinations thereof. In this or another embodiment, the at least one silicon nitride layer described herein have at one least one or more of the following properties: a density of about 2.2 $g/cm^3$ or greater; a hydrogen content of about $4\times10^{22}$ atoms/$cm^3$ or lower, a stress of +50 MPa or greater, a stress change of 300 MPa or less after at least one thermal treatment ranging from about 700 to about 1,000° C., a wet etch rate of 10 nm/min or greater in hot $H_3PO_4$, and combinations thereof.

In one aspect, there is provided an apparatus comprising: a substrate comprising at least one silicon oxide layer; and at least one silicon nitride layer wherein the silicon nitride layer comprises a density of about 2.3 $g/cm^3$ or greater and a hydrogen content of about $4\times10^{22}$ atoms/$cm^3$ or less as measured by an analytical technique such as Fourier transform infrared spectroscopy (FT-IR), Rutherford Backscattering Spectrometry (RBS), or hydrogen forward scattering (HFS) or other method. In one embodiment, the at least one silicon oxide layer and the at least one silicon nitride layer are deposited using the same precursor such as the at least one silicon precursor described herein as a compound having Formulae I through III. In an alternative embodiment, the at least one silicon oxide layer is deposited using a different silicon precursor than the at least silicon nitride layer. In the later embodiment, the at least one silicon nitride layer is deposited using the at least one silicon precursor described herein as a compound having Formulae I through III.

In a further aspect, there is provided an apparatus comprising: a substrate comprising a silicon oxide layer; a silicon nitride layer deposited onto at least a portion of the metal oxide wherein the silicon nitride layer comprises a density of about 2.3 g/cm$^3$ or greater, a hydrogen content of $4\times10^{22}$ atoms/cm$^3$ or less; and a silicon oxide layer deposited between the metal oxide layer and the silicon nitride layer wherein the silicon oxide layer comprises a density of about 2.2 g/cm$^3$ or greater.

In a still further aspect, there is provided a method for depositing a plurality of silicon-containing films selected from at least one silicon oxide layer or at least one silicon nitride layer on at least one surface of a substrate, the method comprising:
  providing the at least one surface of the substrate in a reaction chamber;
  introducing into the reaction chamber at least one silicon precursor selected from the compounds having Formulae I through III wherein R is each independently selected from a hydrogen, linear or branched $C_2$ to $C_{10}$ alkyl group; a linear or branched $C_2$ to $C_{12}$ alkenyl group; a linear or branched $C_2$ to $C_{12}$ alkynyl group; a $C_4$ to $C_{10}$ cyclic alkyl group; and a $C_6$ to $C_{10}$ aryl group; and $R^1$ is each independently selected from a linear or branched $C_1$ to $C_{10}$ alkyl group; a linear or branched $C_3$ to $C_{12}$ alkenyl group; a linear or branched $C_3$ to $C_{12}$ alkynyl group; a $C_4$ to $C_{10}$ cyclic alkyl group; and a $C_6$ to $C_{10}$ aryl group;
  introducing into the reaction chamber a source selected from an oxygen-containing source and a nitrogen-containing source; and
  depositing via a vapor deposition process the silicon-containing layer on the at least one surface of the substrate wherein the vapor deposition process is selected from a group consisting of chemical vapor deposition (CVD), plasma enhanced chemical vapor deposition (PECVD), cyclic chemical vapor deposition (CCVD), plasma enhanced cyclic chemical vapor deposition (PECCVD), atomic layer deposition (ALD), and plasma enhanced atomic layer deposition (PEALD); preferably plasma enhanced chemical vapor deposition (PECVD). In one particular embodiment, the depositing step is conducted at one or more temperatures ranging from about 25° C. to about 1000° C., or from about 400° C. to about 1000° C., or from about 400° C. to about 600° C., or from about 450° C. to about 550° C.

In a still further aspect, there is provided a method for depositing a silicon nitride film on at least one surface of a substrate, the method comprising:
  providing the at least one surface of the substrate in a reaction chamber;
  introducing into the reaction chamber at least one silicon precursor selected from the compounds having Formulae I through III wherein R is each independently selected from a hydrogen, linear or branched $C_2$ to $C_{10}$ alkyl group; a linear or branched $C_2$ to $C_{12}$ alkenyl group; a linear or branched $C_2$ to $C_{12}$ alkynyl group; a $C_4$ to $C_{10}$ cyclic alkyl group; and a $C_6$ to $C_{10}$ aryl group; and $R^1$ is each independently selected from a linear or branched $C_1$ to $C_{10}$ alkyl group; a linear or branched $C_3$ to $C_{12}$ alkenyl group; a linear or branched $C_3$ to $C_{12}$ alkynyl group; a $C_4$ to $C_{10}$ cyclic alkyl group; and a $C_6$ to $C_{10}$ aryl group;
    introducing into the reaction chamber a nitrogen-containing source; and
    depositing via a vapor deposition process the silicon nitride layer on the at least one surface of the substrate wherein the vapor deposition process is selected from a group consisting of chemical vapor deposition (CVD), plasma enhanced chemical vapor deposition (PECVD), cyclic chemical vapor deposition (CCVD), plasma enhanced cyclic chemical vapor deposition (PECCVD), atomic layer deposition (ALD), and plasma enhanced atomic layer deposition (PEALD); preferably plasma enhanced chemical vapor deposition (PECVD). In one particular embodiment, the depositing step is conducted at one or more temperatures ranging from ambient temperature (e.g., about 23° C.) to 1000° C., or from about 400° C. to about 1000° C., or from about 400° C. to about 600° C., or from about 450° C. to about 550° C.

DETAILED DESCRIPTION OF THE INVENTION

Apparatuses or multilayer structures comprising a plurality of silicon oxide films and silicon nitride layers or films such as, for example, 3D VNAND flash memory devices, are being used for many different applications in the electronics industry. In one particular embodiment, these multilayer structures comprise: (i) a silicon nitrogen layer or film which exhibits at least one or more of the following characteristics: a high density (e.g., greater than 2.3 g/cm$^3$ as measured by X-ray reflectivity), a tensile stress of 50 MPa to 300 MPa as measured by the stress tool, a film shrinkage less than 3% and/or a stress drift less than 300 MPa after subjecting to a thermal treatment conducted at one or more temperatures of about 700° C. or greater, a deposition rate of about 50 nm/min or greater, and combinations thereof; and (ii) a silicon oxide layer or film which exhibits at least one or more of the following characteristics: a density of about 1.9 grams per cubic centimeter (g/cm$^3$ or g/cc) or greater, a hydrogen content of $4 \times 10^{22}$ atoms/cm$^3$ or less, a stress of −100 MPa or lower, a dielectric constant of 4.5 or lower, a leakage current of $10^{-9}$ A/cm$^2$ or lower at 8 MV/cm or higher, a film breakdown field of 8 MV/cm or higher, and combinations thereof. In this or other embodiments, the silicon nitride film in the apparatus described herein exhibits substantially or 3% or less, 2% or less, or 1% or less change in one or more of the following properties after subjecting to a high temperature thermal treatment or anneal at one or more of the following temperatures ranging from about 700° C. to about 1,200° C. or from about 700° C. to about 1000° C. In one particular embodiment, the silicon oxide film and the silicon nitride film are formed by a single precursor. In this or other embodiments, the silicon nitride film exhibits a higher wet etch selectivity in hot $H_3PO_4$ than the silicon oxide film, i.e., the silicon nitride film etches much faster than the silicon and oxygen containing film in hot $H_3PO_4$ at temperatures ranging from about 120 to about 200° C., or from about 140 to about 170° C., or from about 160 to about 165° C.

Besides methods using the conventional precursors such as silane ($SiH_4$), there has not been a method described in the art, to deposit multilayer films comprising alternating bilayer structure of a silicon oxide layer and a silicon nitride layer, using a single precursor. One of the challenges in adopting a method using a single precursor for depositing the structure having the silicon oxide layer and the silicon nitride layer is that high quality silicon and oxygen containing films tend to have slightly compressive stress (e.g., ranging from about −300 to about −100 MegaPascals (MPa)). To prevent stress accumulation and stack cracking of the multilayer structure, the silicon nitride film should have a complementary tensile stress (e.g. ranging from about 50 to 300 MPa) to balance out the compressive stress of the silicon oxide layer. However, for most organosilicon precursors and silane based silicon nitride films, the resultant film quality is compromised and may exhibit one or more of the following problems: low density (e.g., 2.2 g/cm$^3$ or less), huge shrinkage after thermal annealing (e.g., greater than 5%, or even greater than 10%), stress increase by 700 MPa to 1 GPa, and combinations thereof. For embodiments wherein the multilayer structure comprising at least one silicon oxide layer and at least one silicon nitride layer is used for 3D VNAND device, the manufacturing process typically contains one or more epi processing steps which are conducted at temperatures of about 700° C. or greater. For these embodiments, the at least one silicon and nitride containing film should withstand thermal treatments at one or more temperatures ranging from about 700° C. to about 1,000° C. This temperature range drastically limits the number of precursors that are suitable.

The method used to form the one or more silicon-containing film(s) or layer(s) are referred to herein as a deposition process. Examples of suitable deposition processes for the method disclosed herein include, but are not limited to, chemical vapor depositions (CVD), cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the films are deposited via atomic layer deposition (ALD), plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can also be liquid or solid which are transported with or without an inert gas into the reactor via direct vaporization, bubbling or sublimation. In some case, the vaporized precursors can pass through a plasma generator. In one embodiment, the one or more films is deposited using an ALD process. In another embodiment, the one or more films is deposited using a CCVD process. In a further embodiment, the one or more films is deposited using a thermal CVD process. The term "reactor" as used herein, includes without limitation, reaction chamber or deposition chamber.

The structure containing silicon-containing layers such as the silicon oxide and silicon nitride layers is deposited using at least one silicon precursor selected from the compounds having Formulae I through III:

wherein R is each independently selected from a hydrogen, linear or branched $C_2$ to $C_{10}$ alkyl group; a linear or branched $C_2$ to $C_{12}$ alkenyl group; a linear or branched $C_2$ to $C_{12}$ alkynyl group; a $C_4$ to $C_{10}$ cyclic alkyl group; and a $C_6$ to $C_{10}$ aryl group; and $R^1$ is each independently selected from a linear or branched $C_1$ to $C_{10}$ alkyl group; a linear or branched $C_3$ to $C_{12}$ alkenyl group; a linear or branched $C_3$ to $C_{12}$ alkynyl group; a $C_4$ to $C_{10}$ cyclic alkyl group; and a $C_6$ to $C_{10}$ aryl group. Exemplary silicon-containing precursors having Formula I to III include, but not limited to, the following compounds below:

Trisilylamine (TSA)   Tri(ethylsilyl)amine

Bis(disilylamino)silane

Bis(bis(ethylsilyl)amino)ethylsilane

Bis[bis(silyl)amino)silyl]methylamine

Bis[bis(ethylsilyl)amino)silyl]ethylamine

In certain embodiments, the method disclosed herein avoids pre-reaction of the precursors by using ALD or CCVD methods that separate the precursors prior to and/or during the introduction to the reactor. In this connection, deposition techniques such as ALD or CCVD processes are used to deposit the film. In one embodiment, the film is deposited via an ALD process by exposing the substrate surface alternatively to the one or more the silicon-containing precursor, oxygen source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

A method for depositing a multilayer structure comprising a silicon-containing layer wherein the silicon-containing layer is selected from a silicon oxide film and a silicon nitride film on at least a surface of a substrate, the method comprising:

providing the at least one surface of substrate;
introducing at least one using at least one silicon-containing precursor selected from the compounds having Formulae I through III wherein R is each independently selected from a hydrogen, linear or branched $C_2$ to $C_{10}$ alkyl group; a linear or branched $C_3$ to $C_{12}$ alkenyl group; a linear or branched $C_3$ to $C_{12}$ alkynyl group; a $C_4$ to $C_{10}$ cyclic alkyl group; and a $C_6$ to $C_{10}$ aryl group; and $R^1$ is each independently selected from a linear or branched $C_1$ to $C_{10}$ alkyl group; a linear or branched $C_3$ to $C_{12}$ alkenyl group; a linear or branched $C_3$ to $C_{12}$ alkynyl group; a $C_4$ to $C_{10}$ cyclic alkyl group; and a $C_6$ to $C_{10}$ aryl group;

introducing into the reaction chamber a source selected from an oxygen-containing source and a nitrogen-containing source; and depositing via a vapor deposition process the silicon-containing layer on the at least one surface of the substrate.

In one particular embodiment, the depositing step is conducted at one or more temperatures ranging from ambient to 1000° C., or from about 400° C. to about 1000° C., or from about 400° C. to about 600° C., 450° C. to about 600° C., or from about 450° C. to about 550° C. In this or other embodiments, the substrate comprises a semiconductor substrate. The oxygen-containing source can be selected from the group consisting of water (H₂O), oxygen (O₂), oxygen plasma, ozone (O₃), NO, N₂O, carbon monoxide (CO), carbon dioxide (CO₂), N₂O plasma, carbon monoxide (CO) plasma, carbon dioxide (CO₂) plasma, and combinations thereof. The nitrogen-containing source can be selected from the group consisting of ammonia, hydrazine, monoalkylhydrazine, dialkylhydrazine, nitrogen, nitrogen plasma, nitrogen/hydrogen, nitrogen/helium, nitrogen/argon plasma, ammonia plasma, ammonia/helium plasma, ammonia/argon plasma, ammonia/nitrogen plasma, NF₃, NF₃ plasma, and mixtures thereof.

In another embodiment, there is provided a method for depositing at least one silicon nitride film on at least a surface of a substrate, the method comprising:

providing the at least one surface of a substrate;

introducing at least one using at least one silicon-containing precursor selected from the compounds having Formulae I through III wherein R is each independently selected from a hydrogen, linear or branched $C_2$ to $C_{10}$ alkyl group; a linear or branched $C_2$ to $C_{12}$ alkenyl group; a linear or branched $C_2$ to $C_{12}$ alkynyl group; a $C_4$ to $C_{10}$ cyclic alkyl group; and a $C_6$ to $C_{10}$ aryl group; and $R^1$ is each independently selected from a linear or branched $C_1$ to $C_{10}$ alkyl group; a linear or branched $C_3$ to $C_{12}$ alkenyl group; a linear or branched $C_3$ to $C_{12}$ alkynyl group; a $C_4$ to $C_{10}$ cyclic alkyl group; and a $C_6$ to $C_{10}$ aryl group;

introducing into the reaction chamber a nitrogen-containing source, or a combination thereof; and depositing via a vapor deposition process the silicon nitride film on the at least one surface of the substrate. In one particular embodiment, the depositing step is conducted at one or more temperatures ranging from ambient to 1000° C., or from about 400° C. to about 1000° C., or from about 400° C. to about 600° C., 450° C. to about 600° C., or from about 450° C. to about 550° C.

A method for forming an apparatus comprising a plurality of silicon-containing layers wherein the silicon-containing layers are selected from a silicon oxide layer and a silicon nitride layer on at least a surface of a semi-conductor substrate, the method comprising:

providing the at least one surface of a semiconductor substrate;

introducing at least one silicon-containing precursor selected from the compounds having the following Formulae I through III:

wherein R is each independently selected from a hydrogen, linear or branched $C_2$ to $C_{10}$ alkyl group; a linear or branched $C_3$ to $C_{12}$ alkenyl group; a linear or branched $C_3$ to $C_{12}$ alkynyl group; a $C_4$ to $C_{10}$ cyclic alkyl group; and a $C_6$ to $C_{10}$ aryl group; and $R^1$ is each independently selected from a linear or branched $C_1$ to $C_{10}$ alkyl group; a linear or branched $C_3$ to $C_{12}$ alkenyl group; a linear or branched $C_3$ to $C_{12}$ alkynyl group; a $C_4$ to $C_{10}$ cyclic alkyl group; and a $C_6$ to $C_{10}$ aryl group;

introducing into the reaction chamber a nitrogen-containing source, or a combination thereof;

depositing via a vapor deposition process the silicon nitride layer;

introducing at least one silicon-containing precursor selected from the group consisting of silane, disilane, tetraethoxysilane (TEOS), triethoxysilane (TES), tetramethoxysilane, trimethoxysilane, di-tert-butoxysilane (DTBOS), di-tert-pentoxysilane (DTPOS), diethylsilane, triethylsilane, diethoxymethylsilane, dimethoxymethylsilane, di(tertiary)butoxymethylsilane, methyltriacetatoxysilane, dimethylacetatoxysilane, dimethyldiacetoxysilane, dimethyldimethoxysilane, dimethyldiethoxysilane, methyltriethoxysilane, neohexyltriethoxysilane, neopentyltrimethoxysilane, diacetoxymethylsilane, phenyldimethoxysilane, phenyldiethoxysilane, phenyltriethoxysilane, phenyltrimethoxysilane, phenylmethyldimethoxysilane, 1,3,5,7-tetramethyltetracyclosiloxane, octamethyltetracyclosiloxane, 1,1,3,3-tetramethyldisiloxane, 1-neohexyl-1,3,5,7-tetramethylcyclotetrasiloxane, hexamethyldisiloxane, 1,3-dimethyl-1-acetoxy-3-ethoxydislioxane, 1,2-diemthyl-1,2-diacetoxy-1,2-diethoxydisilane, 1,3-dimethyl-1,3-diethoxydisiloxane, 1,3-dimethyl-1,3-diacetoxydisilxane, 1,2-dimethyl,1,1,2,2-tetraacetoxydisilane, 1,2-dimethyl-1,1,2,2-tetraethoxydisilane, 1,3-dimethyl-1-acetoxy-3-ethoxydisiloxane, 1,2-dimethyl-1-acetoxy-2-ethoxydisilane, methylacetoxy(tertiary)butoxysilane, methylsilane, dimethylsilane, trimethylsilane, tetramethylsilane, hexamethyldisilane, tetramethyldisilane, and dimethyldisilane, hexamethyldisiloxane (HMDSO), octamethylcyclotetrasiloxane (OMCTS) and tetramethylcyclotetrasiloxane (TMCTS)), bis(triethoxysilyl)methane, bis(triethoxysilyl)ethane, bis(trimethoxysilyl)methane, bis(trimethoxysilyl)ethane, bis(diethoxymethylsilyl)methane, bis(diethoxymethylsilyl)ethane, bis(methyldiethoxysilyl)methane, (diethoxymethylsilyl)(diethoxysilyl)methane and combinations thereof, introducing into the reaction chamber an oxygen-containing source, or a combination thereof; and depositing via a vapor deposition process the silicon oxide layer. In one particular embodiment, the depositing step is conducted at one or more temperatures ranging from ambient to 1000° C., or from about 400° C. to about 1000° C., or from about 400° C. to about 600° C., 450° C. to about 600° C., or from about 450° C. to about 550° C. In another particular embodiment, the depositing step is conducted with the silicon oxide being deposited before the silicon nitride. The depositing steps can be repeated to provide multilayer stack of alternating silicon nitride and silicon oxide.

In the formulas above and throughout the description, the term "alkyl" denotes a linear, or branched functional group having from 2 to 10 or 2 to 4 carbon atoms. Exemplary alkyl groups include, but are not limited to, ethyl, n-propyl, isopropyl, n-butyl, isobutyl, sec-butyl, tert-butyl, n-pentyl, iso-pentyl, tert-pentyl, hexyl, isohexyl, and neohexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto.

In the formulas above and throughout the description, the term "cyclic alkyl" denotes a cyclic functional group having from 3 to 10 or from 4 to 10 carbon atoms. Exemplary cyclic alkyl groups include, but are not limited to, cyclobutyl, cyclopentyl, cyclohexyl, and cyclooctyl groups.

In the formulas above and throughout the description, the term "aryl" denotes an aromatic cyclic functional group having from 6 to 10 carbon atoms. Exemplary aryl groups include, but are not limited to, phenyl, benzyl, chlorobenzyl, tolyl, and o-xylyl.

In the formulas above and throughout the description, the term "alkenyl group" denotes a group which has one or more carbon-carbon double bonds and has from 2 to 10 or from 2 to 6 carbon atoms. Exemplary alkenyl groups include, but are not limited to, vinyl or allyl groups In the formulas above and throughout the description, the term "alkynyl group" denotes a group which has one or more carbon-carbon triple bonds and has from 2 to 10 or from 2 to 6 carbon atoms.

In certain embodiments, the substrate comprises a semiconductor substrate. Throughout the description, the term "semi-conductor substrate" denotes a substrate comprising silicon, germanium, silicon oxide, silicon nitride, silicon carbide, silicon carbonitride, carbon doped silicon oxide, boron doped silicon, phosphorous doped silicon, boron doped silicon oxide, phosphorous doped silicon oxide, boron doped silicon nitride, phosphorous doped silicon nitride, metal such as copper, tungsten, aluminum, cobalt, nickel, tantalum), metal nitride such as titanium nitride, tantalum nitride, metal oxide, III/V such as GaAs, InP, GaP, and GaN, and a combination thereof.

Figure 1:
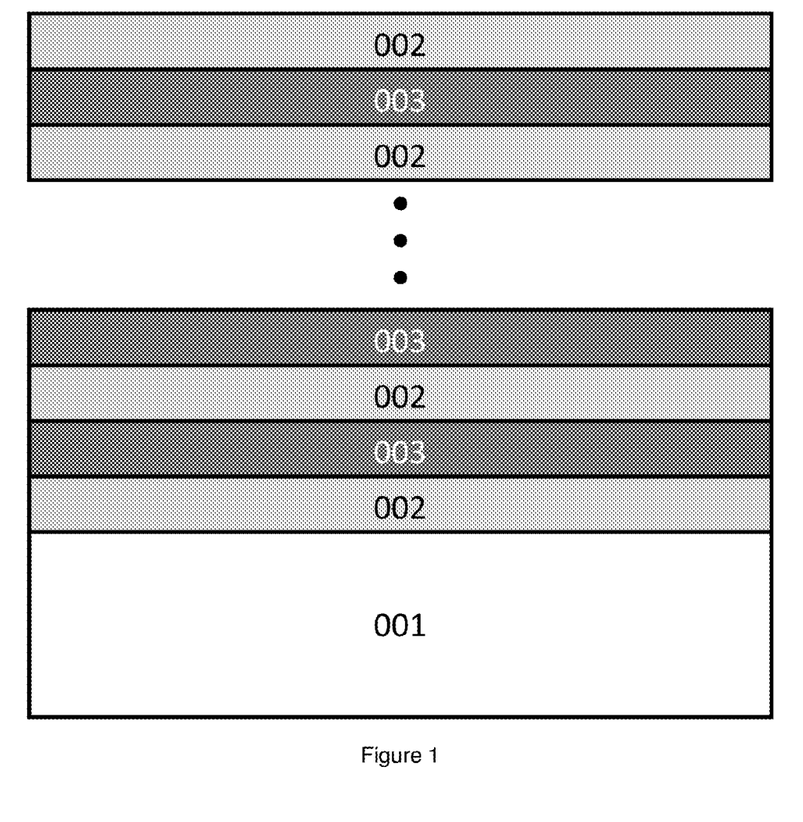
FIG. 1 shows an embodiment of the apparatus or multi-layer structure comprising alternating silicon oxide layers (002) and silicon nitride layers (003) on a semiconductor substrate (001).
Figure 2:
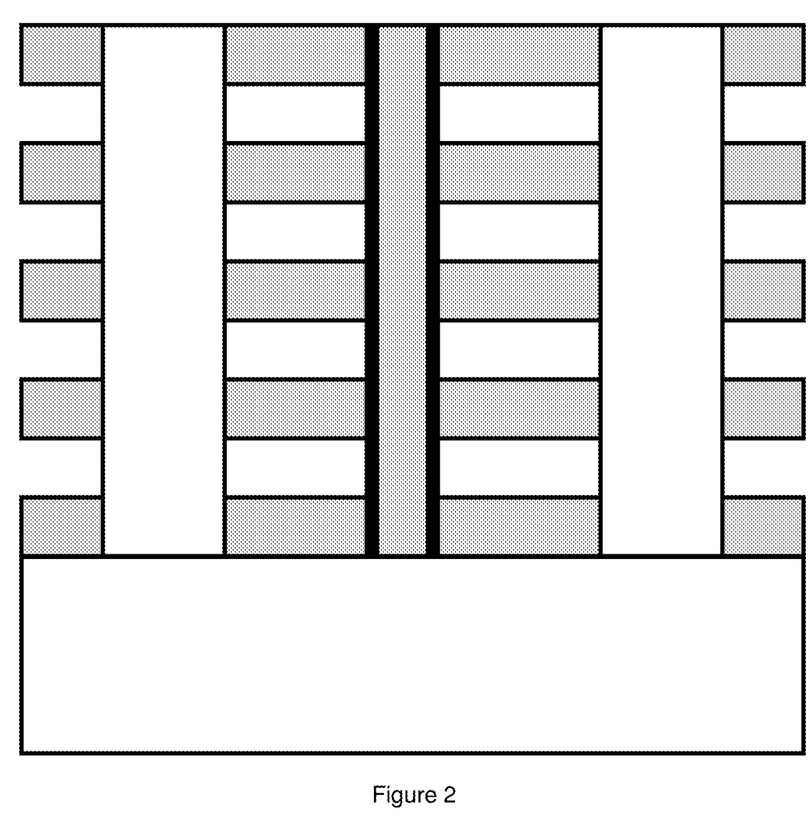
FIG. 2 shows the removal of the sacrificial silicon nitride layers by hot $H_3PO_4$ etching after trench etching and ploy Si growth.

In certain embodiments, the silicon-containing film or layer deposited using the methods described herein are formed in the presence of oxygen using an oxygen source, reagent or precursor comprising oxygen to provide a silicon oxide film. The term "silicon oxide" film means a stoichiometric or non-stoichiometric film comprised of silicon and oxygen. FIG. 1 provides an example of a multilayer apparatus described herein. In FIG. 1, the silicon oxide films (002) deposited using the methods described above are formed in the presence of oxygen using an oxygen source, reagent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), NO, $N_2O$, carbon monoxide (CO), carbon dioxide ($CO_2$) and combinations thereof. In one particular embodiment, the oxygen source gas comprises nitrous oxide ($N_2O$). In this or other embodiments, the oxygen source is introduced into the reactor at a flow rate ranging from about 1 to about 4000 square cubic centimeters (sccm).

In certain embodiments, the silicon-containing films comprise silicon and nitrogen to provide a silicon nitride film. The term "silicon nitride" film means a stoichiometric or non-stoichiometric film comprised of silicon and nitrogen. In these embodiments, the silicon-containing films deposited using the methods described herein are formed in the presence of nitrogen-containing source. In one particular embodiment such as that depicted in FIG. 1, the silicon-containing film 003 comprises silicon nitride and is deposited using the methods described above in the presence of nitrogen using a nitrogen, reagent or precursor comprising nitrogen. A nitrogen-containing source may be introduced into the reactor in the form of at least one nitrogen source and/or may be present incidentally in the other precursors used in the deposition process. Suitable nitrogen-containing source gases may include, for example, ammonia, hydrazine, monoalkylhydrazine, dialkylhydrazine, nitrogen, nitrogen plasma, nitrogen/hydrogen, nitrogen/helium, nitrogen/argon plasma, ammonia plasma, ammonia/helium plasma, ammonia/argon plasma, ammonia/nitrogen plasma, $NF_3$, $NF_3$ plasma, and mixtures thereof. In certain embodiments, the nitrogen-containing source comprises an ammonia plasma or hydrogen/nitrogen plasma source gas that is introduced into the reactor at a flow rate ranging from about 1 to about 4000 square cubic centimeters (sccm). The nitrogen-containing source can be introduced for a time that ranges from about 0.1 to about 100 seconds. In one particular embodiment the deposition rate for the silicon oxide film using the compounds having the following Formulae I through III ranges from about 50 nanometers per minute (nm/min) to about 500 nm/min which is higher than the deposition rate of silicon oxide with similar properties using silane under same conditions. In another particular embodiment the deposition rate for the silicon nitride film ranges from about 50 nanometers per minute (nm/min) to about 500 nm/min which is higher than the deposition rate of silicon nitride with similar properties using silane under same conditions.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon (Ne), hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, the oxygen-containing source, the nitrogen-containing source, and/or other precursors, source gases, and/or reagents may be performed by changing the time for supplying them to change the stoichiometric composition of the resulting film.

Energy is applied to the at least one of the silicon-containing precursor, oxygen-containing source, nitrogen-containing source, reducing agent, other precursors and/or combination thereof to induce reaction and to form the silicon-containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The silicon-containing precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

In certain embodiments, the gas lines connecting from the precursor canisters to the reaction chamber are heated to one or more temperatures depending upon the process requirements and the container of the at least one silicon-containing precursor is kept at one or more temperatures for bubbling. In other embodiments, a solution comprising the at least one silicon-containing precursor is injected into a vaporizer kept at one or more temperatures for direct liquid injection.

For those embodiments wherein the silicon-containing precursor(s) having formulae I to III described is used in a composition further comprising a solvent, the solvent or mixture thereof selected does not react with the precursor(s). The amount of solvent by weight percentage in the composition ranges from 0.5% by weight to 99.5% or from 10% by weight to 75%. In this or other embodiments, the solvent has a boiling point (b.p.) similar to the b.p. of the precursor or the difference between the b.p. of the solvent and the b.p. of the precursor is 40° C. or less, 30° C. or less, or 20° C. or less, or 10° C. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkyl hydrocarbon (such as octane, nonane, dodecane, ethylcyclohexane), an aromatic hydrocarbon (such as toluene, mesitylene), a tertiary aminoether (such as bis(2-dimethylaminoethyl) ether), or mixtures thereof.

In one particular embodiment, the silicon-containing precursor(s) having formulae I to III may contain halide ions (or halides) such as, for example, chlorides and fluorides, bromides, and iodides which are 500 parts per million (ppm) or less, 100 ppm or less, 50 ppm or less, 10 ppm or less, and 5 ppm or less of the impurity or 0 ppm. Chlorides are known to act as decomposition catalysts for the silicon-containing precursor(s) having formulae I to III as well as potential contaminate to detrimental to performance of electronic device. The gradual degradation of the silicon-containing precursor(s) having formulae I to III described may directly impact the film deposition process making it difficult for the semiconductor manufacturer to meet film specifications. In addition, the shelf-life or stability is negatively impacted by the higher degradation rate of the silicon-containing precursor(s) having formulae I to III, thereby making it difficult to guarantee a 1-2 year shelf-life. Therefore, the accelerated decomposition of the silicon-containing precursor(s) having formulae I to III presents safety and performance concerns related to the formation of these flammable and/or pyrophoric gaseous byproducts.

Compositions according to the present invention that are substantially free of halides can be achieved by (1) reducing or eliminating chloride sources during chemical synthesis, and/or (2) implementing an effective purification process to remove chloride from the crude product such that the final purified product is substantially free of chlorides. Chloride sources may be reduced during synthesis by using reagents that do not contain halides such as chlorodislanes, bromodisilanes, or iodisilanes thereby avoiding the production of by-products that contain halide ions. In addition, the aforementioned reagents should be substantially free of chloride impurities such that the resulting crude product is substantially free of chloride impurities. In a similar manner, the synthesis should not use halide based solvents, catalysts, or solvents which contain unacceptably high levels of halide contamination. The crude product may also be treated by various purification methods to render the final product substantially free of halides such as chlorides. Such methods are well described in the prior art and, may include, but are not limited to, purification processes such as distillation, or adsorption. Distillation is commonly used to separate impurities from the desire product by exploiting differences in boiling point. Adsorption may also be used to take advantage of the differential adsorptive properties of the components to effect separation such that the final product is substantially free of halide. Adsorbents such as, for example, commercially available $MgO$—$Al_2O_3$ blends can be used to remove halides such as chloride.

In another embodiment, a vessel for depositing a silicon-containing film comprising one or more silicon-containing precursor having Formulae I to III are described herein. In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the precursor is provided in a pressurizable vessel comprised of stainless steel and the purity of the precursor is 98% by weight or greater or 99.5% or greater which is suitable for the majority of semiconductor applications. In certain embodiments, such vessels can also have means for mixing the precursors with one or more additional precursor if desired. In these or other embodiments, the contents of the vessel(s) can be premixed with an additional precursor. Alternatively, the silicon-containing precursor can be maintained in separate vessels or in a single vessel having separation means for maintaining the precursor and other precursor separate during storage.

In the method described herein, it is understood that the steps of the methods described herein may be performed in a variety of orders, may be performed sequentially or concurrently (e.g., during at least a portion of another step), and any combination thereof. The respective step of supplying the precursors and the oxygen-containing source or nitrogen-containing source gases may be performed by varying the duration of the time for supplying them to change the stoichiometric composition of the resulting silicon-containing film. In certain embodiments, such as the apparatus shown in FIG. 1, silicon-containing layers 002 and 003 are deposited using the same silicon-containing precursor such as the compounds described herein having Formulae I through III. The silicon-containing layer or film 002 comprises silicon and oxygen which is formed in the presence of an oxygen-containing source. An oxygen-containing source may be introduced into the reactor in the form of at least one oxygen source and/or may be present incidentally in the other precursors used in the deposition process. The silicon-containing film 003 comprises silicon and nitrogen which is deposited using the methods described above in the presence of nitrogen using a nitrogen source, reagent or precursor comprising nitrogen. The thickness of silicon oxide ranges from 1 Å to 5000 Å, 10 Å to 2000 Å, 50 Å to 1500 Å, 50 Å to 1000 Å, 50 Å to 500 Å whereas the thickness of silicon nitride ranges from 1 Å to 5000 Å, 10 Å to 2000 Å, 50 Å to 1500 Å, 50 Å to 1000 Å, 50 Å to 500 Å depending on the number of layers. The thickness of the one or more silicon oxide film or layer may be the same as or different than the thickness of the silicon nitride film or layer. Thickness of the layers can be measured, for example, by ellipsometer, refractometer, or other means. In one embodiment, the difference in thickness measurement of the silicon oxide layer and the silicon nitride layer, measured in + or − percentage of thickness, ranges from one or more of the following endpoints: +/−0.001, 0.005, 0.01, 0.05, 0.1, 0.5, 1, 2, 2.5, 5, 10, 25, 50 and 100%. For example, if the silicon oxide layer is 20 nanometers and the silicon nitride layer is 20.5 nanometers, then the difference in thickness would be 0.025%. In one particular embodiment, the difference in thickness between the silicon oxide layer and silicon nitride layer ranges from about ±0.001% to about ±10% or from about ±0.01% to about ±5%.

In certain embodiments, such as the apparatus shown in FIG. 1, the apparatus is subjected to one or more post-treatment step(s) including, but not limited to, a thermal treatment of annealing step at one or more temperatures ranging from about 600° C. to about 1000° C., or about 700° C. to 1000° C. The post-treatment step can be conducted using one or more of the following energy sources: UV, infrared, plasma, or any other energy sources. In embodiments wherein the apparatus is subjected to a post-treatment step such as annealing, the percentage of shrinkage before and after the post-treatment step should be 5% or less, <2% or less, 0.5% or less, or zero for the silicon and oxygen containing layer (such as, for example layer 002 in FIG. 1) and the percentage of shrinkage before and after the post-treatment step should be 10% or less, 5% or less, and 3% or less, or 2% for silicon and nitrogen containing layer (such as, for example layer 003 in FIG. 1). To avoid the structure cracking and keep the stack stress low, the stress increase of silicon and oxygen containing film 002 should be 50 MPa or less; the stress increase of silicon and nitrogen containing film 003 should be 300 MPa or less, preferably 200 MPa or less.

The temperature of the reactor or deposition chamber for the deposition may range from one of the following endpoints: ambient temperature or 25° C.; 400° C.; 425° C.; 475° C.; 500° C.; 525° C.; 550° C.; 575° C.; 600° C.; 625° C.; 650° C.; 700° C., 1000° C. and any combinations thereof. In this regard, the temperature of the reactor or deposition chamber for the deposition may range from ambient temperature to 1000° C., from about 400° C. to about 700° C., from about 400° C. to about 600° C., from about 450° C. to 550° C., or any combinations of the temperature end-points described herein.

The pressure of the reactor or deposition chamber may range from about 0.01 Torr to about 1000 Torr, or from about 0.1 Torr to about 100 Torr. The respective step of supplying the precursors, the oxygen source, the nitrogen source, and/or other precursors, source gases, and/or reagents may be performed by changing the time for supplying them to change the stoichiometric composition of the resulting silicon-containing film.

The following examples illustrate the method for preparing a silicon-containing film described herein or apparatus comprising same and are not intended to limit it in any way. The examples and embodiments described herein, are exemplary of numerous embodiments that may be made. It is contemplated that numerous materials other than those specifically disclosed may be made. Numerous other configurations of the process may also be used, and the materials used in the process may be elected from numerous materials other than those specifically disclosed.

EXAMPLES

General Deposition Conditions

The silicon containing films were deposited onto medium resistivity (8-12 Ωcm) single crystal silicon wafer substrates. In certain examples, the substrate may be exposed to a pre-deposition treatment such as, but not limited to, a plasma treatment, thermal treatment, chemical treatment, ultraviolet light exposure, electron beam exposure, and/or other treatments to affect one or more properties of the film. This allows for the dielectric properties to be preserved or enhanced prior to film deposition.

The depositions in Examples 1 through 9 were performed on an Applied Materials Precision 5000 system in a 200 mm DXZ chamber fitted with an Astron EX remote plasma generator, using either a silane or a TEOS process kit. The PECVD chamber was equipped with direct liquid injection delivery capability. With the exception of silane, all precursors were liquids with delivery temperatures dependent on the precursor's boiling point. Typical liquid precursor flow rates were 100-800 mg/min, plasma power density was 0.75-3.5 W/cm², pressure was 0.75-10 Torr. Thickness and refractive index (RI) at 632 nm were measured by a reflectometer or ellipsometer. Typical film thickness ranged from 10 to 1000 nm. Bonding properties hydrogen content (Si—H, C—H and N—H) of the silicon-based films were measured and analyzed by a Nicolet transmission Fourier transform infrared spectroscopy (FTIR) tool. All density measurements were accomplished using X-ray reflectivity (XRR). X-ray Photoelectron Spectroscopy (XPS) and Secondary ion mass spectrometry (SIMS) analysis were performed to determine the elemental composition of the films. Wet etch rate (WER) was measured in hot $H_3PO_4$ (160~165° C.). A mercury probe was adopted for the electrical properties measurement including dielectric constant, leakage current and breakdown field. The stress of the film was measured by Toho FLX-2320 stress tool. The films were annealed at 650~800° C. for 1 hour in $N_2$ ambient ($O_2$<10 ppm) from 1 Torr to atmospheric pressure; then film shrinkage, stress drift, WER, film density and elemental composition were analyzed. The multilayer structures and interfaces were observed using a Hitachi S-4700 Scanning Electron Microscopy (SEM) system at a resolution of 2.0 nm.

Silicon precursors were screened using a design of experiment (DOE) methodology. The experimental design for silicon and oxygen containing films includes: precursor flow from 100 to 800 mg/min; $O_2$ (or $N_2O$) flow from 100 sccm to 4000 sccm, pressure from 0.75 to 8 torr; RF power (13.56 MHz) 400 to 1000 W; Low-frequency (LF) power 0 to 100 W; and deposition temperature ranged from 150 to 550° C. The experimental design for silicon and nitrogen containing films includes: precursor flow from 100 to 800 mg/min; $NH_3$ flow from 100 sccm to 4000 sccm, pressure from 0.75 to 8 torr; RF power (13.56 MHz) 400 to 1000 W; Low-frequency (LF) power 0 to 100 W; and deposition temperature ranged from 150 to 550° C. The DOE experiments were used to determine what process parameters produced the optimal film with high densities and good thermal stability.

Example 1: Deposition of Silicon and Oxygen Containing Films Using Trisilylamine (TSA) and Nitrous Oxide ($N_2O$)

A number of silicon oxide films were deposited using trisylamine (TSA) as a precursor onto 6 inch and 8 inch silicon substrates to test the film density, stress, thermal stability and wet etch rate. The composition of the films were measured by XPS and showed that the films were comprised of SiO wherein the amount of silicon and oxygen varied in atomic percentage depending upon the film.

Of the oxide films deposited by TSA, the process conditions used to deposit the silicon-containing films showing the most favorable film properties using TSA were as follows: TSA flow (200-300 mg/min), $N_2O$ flow (2000~4000 sccm), He (1000 sccm), Pressure (4~6 torr), RF (600~900 W), and Temperature (425° C.). Table 1 shows the deposition conditions for a selected silicon oxide deposition using TSA:

TABLE 1

| Power (W) | Spacing (mils) | Pressure (Torr) | TSA (mg/min) | He (sccm) | $N_2O$ (sccm) | Deposition (Dep) Temp (° C.) |
|---|---|---|---|---|---|---|
| 600 | 300 | 4 | 250 | 1000 | 3000 | 425 |

Figure 3:
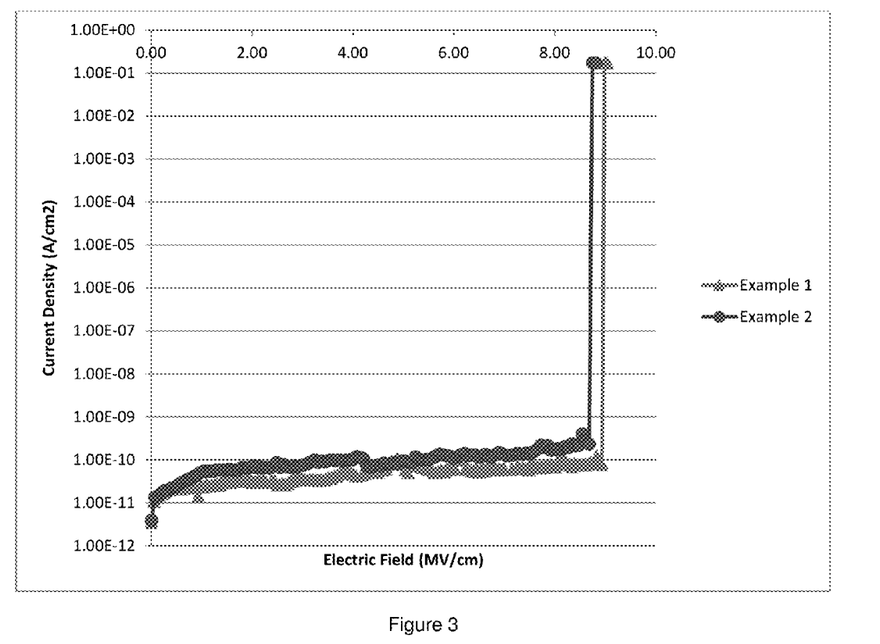
FIG. 3 shows leakage current and breakdown voltage of two exemplary TSA-deposited silicon oxide containing films in Example 1. The films showed low leakage current and high breakdown field; any noises shown in the figure are due to tool instability.

The deposition rate was 126 nm/min. The as-deposited film stress was −283 MPa. The dielectric constant of 4.20 and density of 2.24 g/cm³ indicate it is a high quality silicon oxide film. XPS elemental analysis indicates the Si:O ratio is 1:2. The leakage and breakdown measurement, as depicted in FIG. 3, shows that the leakage current is below $10^{-9}$ A/cm², and breakdown field greater than 8 MV/cm, indicating excellent insulating properties. The silicon oxide film shows excellent thermal stability. After 800° C. annealing in $N_2$ ambient for 1 hour, the film shrinkage was negligible, or was substantially zero, and the stress shift was approximately 50 MPa.

Example 2: Deposition of Silicon and Oxygen Containing Films Using Trisilylamine (TSA) and Nitrous Oxide ($N_2O$)

A number of silicon oxide films were deposited using trisylamine (TSA) as a precursor onto 6 inch and 8 inch silicon substrates to test the film density, stress, thermal stability and wet etch rate. The parameters used to deposit the films are provided below in Table 2.

TABLE 2

| Power (W) | Spacing (mils) | Pressure (Torr) | TSA (mg/min) | He (sccm) | $N_2O$ (sccm) | Dep Temp (° C.) |
|---|---|---|---|---|---|---|
| 800 | 300 | 4 | 250 | 1000 | 2000 | 425 |

The deposition rate was 100 nm/min. The as-deposited film stress was −313 MPa. The dielectric constant of 4.14 and density of 2.36 g/cm³ indicate it is a high quality silicon oxide film. XPS elemental analysis indicates the Si:O ratio is 1:2. The leakage and breakdown measurement, as depicted in FIG. 3, shows that the leakage current is below $10^{-9}$ A/cm², and breakdown field greater than 8 MV/cm, indicating excellent insulating properties.

The silicon oxide film showed excellent thermal stability. After 800° C. annealing in $N_2$ ambient for 1 hour, the film shrinkage was negligible and stress shift was approximately 50 MPa. Both silicon oxide films in Example 1 and Example 2 also showed substantially zero wet etch rate in hot $H_3PO_4$ at 160~165° C.

Example 3: Deposition of Silicon Nitride Films Using Trisilylamine (TSA) and Ammonia ($NH_3$)

A number of silicon nitride films were deposited using trisylamine (TSA) as a precursor onto 6 inch and 8 inch silicon substrates to test the film density, stress, thermal stability and wet etch rate. The composition of the films were measured by XPS and showed that the films were comprised of silicon nitride wherein the amount of silicon and nitride varied in atomic percentage depending upon the film.

Of the nitride films deposited by TSA, the process conditions used to deposit the silicon-containing films showing the most favorable film properties using TSA were as follows: TSA flow (150 mg/min), $NH_3$ flow (600~1000 sccm), He (1000 sccm), Pressure (4-8 torr), RF (600~900 W), and Temperature (425° C.). Table 3 shows the deposition conditions for a selected silicon nitride deposition using TSA. The deposition rate was 298 nm/min.

TABLE 3

| Power (W) | Spacing (mils) | Pressure (Torr) | TSA (mg/min) | He (sccm) | $NH_3$ (sccm) | Deposition Temperature (° C.) |
|---|---|---|---|---|---|---|
| 800 | 500 | 5 | 150 | 1000 | 1000 | 425 |

By measuring film thickness and stress before and after 800° C. thermal annealing in $N_2$ ambient for 1 hour, it was found that these silicon nitride films were stable and resistant to high temperature treatment, as shown in the following Table 4.

TABLE 4

| As dep. stress (MPa) | Post anneal stress (MPa) | Δ stress (MPa) | Thickness Shrinkage |
|---|---|---|---|
| 108 | 265 | 157 | 1.4% |

The stress of the as-deposited film is slightly tensile, which balances out the compressive stress of the oxide layer. The stress of the post-annealed film increased by 157 MPa and the film shrinkage was about 1.4%, both of which assure the good thermal stability of the silicon nitride film. The wet etch rates of the as-deposited and post-annealed films in hot $H_3PO_4$ at 160~165° C. were ~120 and ~30 nm/min, respectively. The nitride films etched much faster than oxide films, showing good etch selectivity.

Example 4: Deposition of Silicon Oxide/Nitride Film Stacks Using Trisilylamine (TSA)

A stack comprising 25 nm silicon oxide and 25 nm silicon nitride films were deposited on a 200 mm silicon substrate to provide a multilayer stack in an alternating sequence using the precursor trisilyamine (TSA)+nitrous oxide ($N_2O$) to form the silicon oxide layer and TSA+ammonia ($NH_3$) to form the silicon nitride layer. The single layer oxide film stress was −294 MPa and the single layer nitride film stress was 231 MPa. The deposition conditions for silicon oxide film and silicon nitride film are listed in Table 5.

TABLE 5

|         | Power (W) | Pressure (Torr) | TSA flow (mg/min) | He carrier (sccm) | $N_2O$ flow (sccm) | $NH_3$ flow (sccm) | Temperature (° C.) |
|---------|-----------|-----------------|-------------------|-------------------|--------------------|--------------------|--------------------|
| Oxide   | 900       | 4               | 250               | 1000              | 2000               |                    | 425                |
| Nitride | 900       | 5               | 150               | 1000              |                    | 1000               | 425                |

The stack stress was measured after 8, 16, 32, 64 and 128 stack layers deposition. The stress slightly increased with the stack thickness, as shown in Table 6.

TABLE 6

| # of Stacks                       | Film Stress (MPa) |
|-----------------------------------|-------------------|
| 8 bi-layer stacks (16 total layers)   | −66  |
| 16 bi-layer stacks (32 total layers)  | −58  |
| 32 bi-layer stacks (64 total layers)  | −57  |
| 64 bi-layer stacks (128 total layers) | −36  |
| 128 bi-layer stacks (256 total layers)| −51  |

Figure 4:
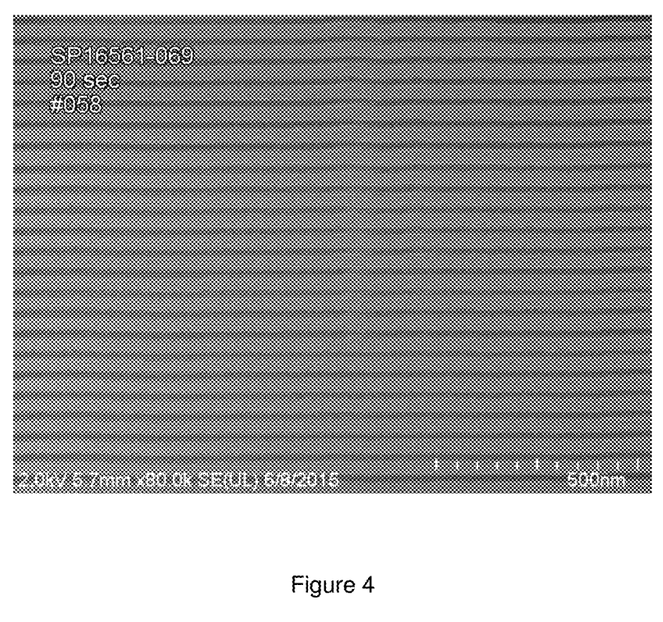
FIG. 4 provides a scanning electron microscope (SEM) image of the 128 stacks of alternating silicon oxide and silicon nitride layers in Example 4 which shows that the interfaces between the oxide and nitride layers are clear and distinct.
Figures 5A, 5B:
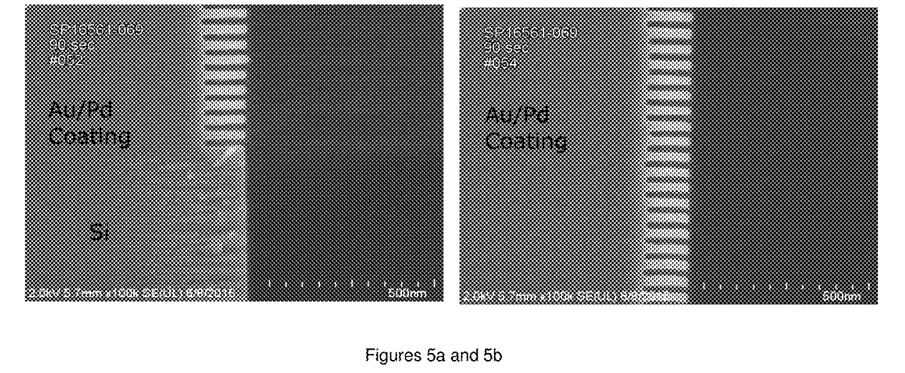
FIGS. 5a and 5b provides SEM images of different views of the 128 stacks of alternating silicon oxide and silicon nitride layers in Example 4 after immersing the stack in a hot (160~165° C.) $H_3PO_4$ bath for 90 seconds to remove the silicon nitride layers, demonstrating that the silicon nitride layers can be selectively removed.

FIG. 4 provides a scanning electron microscope (SEM) image of the 128 stack of alternating silicon oxide and silicon nitride layers, demonstrating the interfaces between the oxide and nitride layers are clear and distinct. The multilayer structure of 128 stacks was then immersed into a hot (160~165° C.) $H_3PO_4$ bath for 90 seconds. Images of the multilayer structure after the hot $H_3PO_4$ bath were taken at a resolution of 500 nm by SEM and are shown as FIGS. 5a and 5b showing the excellent etch selectivity and distinct interface between oxide and nitride layers.

Example 5: Deposition and Thermal Annealing of Silicon Oxide/Nitride Film Stacks Using Trisilylamine (TSA)

A 128 stack layer structure containing alternating layers of 25 nm silicon oxide and 25 nm silicon nitride films was deposited on a 150 mm silicon substrate using TSA+nitrous oxide ($N_2O$) for the silicon oxide layers and TSA+ammonia ($NH_3$) for the silicon nitride layers. The stress of the as-deposited stack was measured and the results are provided in Table 7. As Table 7 shows, the multilayered structures exhibited slightly compressive stress and the stress slightly increased with the stack thickness. The stack was loaded into a tube furnace and annealed at 800° C. in $N_2$ ambient for 1 hour. The stress change of the stacks after annealing was approximately 115 MPa and is provided in Table 7.

TABLE 7

| # of Stacks | As-dep. Stress (MPa) | Post-annealed stress (MPa) | Δ Stress (MPa) |
|---|---|---|---|
| 8 (16 total layers, 400 nm)    | −62 | N/A | N/A |
| 16 (32 total layers, 800 nm)   | −56 | N/A | N/A |
| 32 (64 total layers, 1600 nm)  | −54 | N/A | N/A |
| 64 (128 total layers, 3200 nm) | −49 | N/A | N/A |
| 128 (256 total layers, 6400 nm)| −46 | 69  | 115 |

Example 6: Deposition and Thermal Annealing of Silicon Oxide/Nitride Film Stacks Using Trisilylamine (TSA) with Different Thicknesses A 64 stack layer structure containing alternating layers of 20 nm silicon oxide and 30 nm silicon nitride films were deposited on a 150 mm silicon substrate using TSA+nitrous oxide ($N_2O$) for the silicon oxide layers and TSA+ammonia ($NH_3$) for the silicon nitride layers. The stress of the as-deposited stack and post-annealed stack was measured and the results are provided in Table 8. Since the nitride film has a higher stress than the oxide film, with thicker nitride layers, the stress of this stack is higher than the stack with 25 nm oxide/25 nm nitride in Example 5.

TABLE 8

| # of Stacks | As-dep. stress (MPa) | Post-annealed Stress (MPa) | Δ Stress (MPa) |
|---|---|---|---|
| 8 (16 total layers, 400 nm)    | −40 | N/A | N/A |
| 16 (32 total layers, 800 nm)   | −29 | N/A | N/A |
| 32 (64 total layers, 1600 nm)  | −28 | N/A | N/A |
| 64 (128 total layers, 3200 nm) | −19 | 95  | 114 |

Example 7: Deposition and Thermal Annealing of TEOS Silicon Oxide/TSA Silicon Nitride Film Stacks A 64 stack layer structure was deposited containing alternating layers of 20 nm silicon oxide films using tetraethyl orthosilicate (TEOS) and 30 nm silicon nitride films deposited using trisilylamine (TSA). The stress of the as-deposited stack and post-annealed stack was measured and the results are provided in Table 9. The as-deposited TEOS oxide film showed slightly compressive stress of −97 MPa and it decreased to −168 MPa after 800° C. annealing. As a result, the decrease of TEOS oxide stress compensated for the increase of TSA nitride stress. As a result, the stress of the stack did not change by a great amount.

TABLE 9

| # of Stacks | As-dep. Stress (MPa) | Post-annealed Stress (MPa) | Δ Stress (MPa) |
|---|---|---|---|
| 8 (16 total layers, 400 nm)    | 150 | N/A | N/A |
| 16 (32 total layers, 800 nm)   | 131 | N/A | N/A |
| 32 (64 total layers, 1600 nm)  | 122 | N/A | N/A |
| 64 (128 total layers, 3200 nm) | 131 | 125 | −7  |

Example 8: Deposition and Thermal Annealing of Silane Based Silicon Nitride Films Silane based nitride was deposited on 200 mm silicon wafers. Preferred deposition conditions include: silane flow from 50 to 100 sccm; NH$_3$ flow from 100 sccm to 1000 sccm, N$_2$ flow from 500 to 2000 sccm, pressure from 2 to 4 torr; RF power (13.56 MHz) 200 to 600 W; and deposition temperature ranged from 400 to 500° C. The film stress, density, and thickness shrinkage are listed in Table 10.

TABLE 10

| Wafer # | Stress (MPa) | Density (g/cm$^3$) | Film Shrinkage (800° C. annealing) |
|---|---|---|---|
| W6 | −460 | 2.62 | 2.69% |
| W9 | 40 | 2.46 | 7.86% |
| W16 | 60 | 2.48 | 9.55% |

The silicon nitride film density was compromised by the tensile stress requirement. The silane based nitride films showed similar density to TSA nitride with slightly different tensile stress. However, the silane based nitride showed much greater film shrinkage; as a result the stress change can be up to 1 GPa or higher, implying that silane based nitride may not be suitable for the V-NAND application as the number of stacks increases, such as greater than 50 stacks.

Example 9: Reduction of Nitrogen Concentration in Oxide Layer at the Interface Between Silicon Nitride and Silicon Substrate The silicon oxide film was deposited on a silicon wafer with the oxide deposition conditions in Table 5. The nitrogen (N) content of the silicon oxide film was detected by Dynamic SIMS. The N content was low in the silicon oxide film, at 1E20 atoms/cc. However, there was a sudden N concentration increase at the interface between the oxide film and silicon substrate, where the N concentration is up to 1E22 atoms/cc which can potentially change the etching rate.

To lower the N concentration at the interface, the silicon oxide deposition recipe was broken into two steps. In the first step, N$_2$O was flowed at 4000 sccm for 4~5 seconds to fully oxidize the precursor and in the second step it was reduced to 2000 sccm. The nitrogen content was evaluated by dynamic SIMS. The N level was at 1E20 atoms/cc level throughout the film; no sudden increase was seen at the interface.

Figure 6:
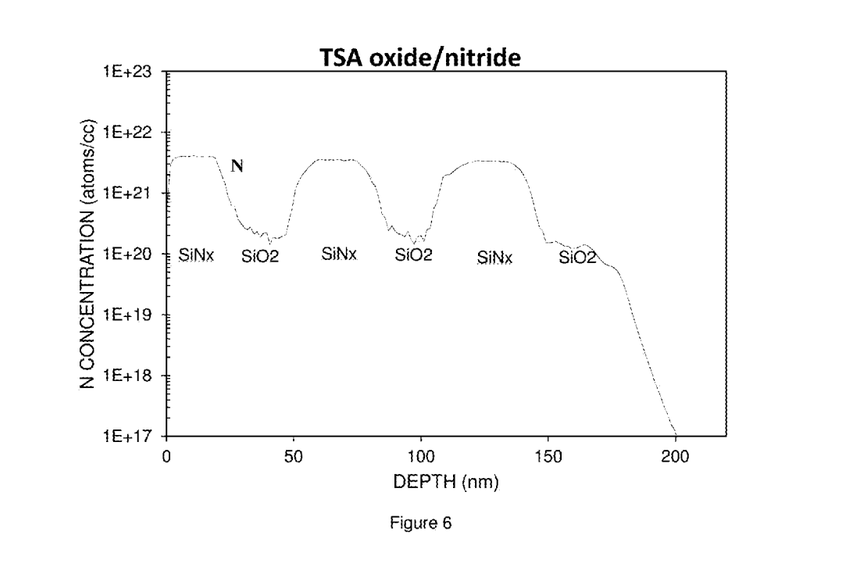
FIG. 6 shows the dynamic SIMS profile of the nitrogen concentration in the three bilayer structure of oxide/nitride on a silicon substrate in Example 9.

Silicon oxide/nitride stack structures were deposited using the modified oxide recipe and the nitride recipe in Table 5. Each layer was 25~30 nm thick. By dynamic SIMS analysis of N concentration, the N concentration profile is shown in FIG. 6. It can be seen that in the silicon oxide layers, the N content is at the level of 1E20 atoms/cc; while in the silicon nitride layers, the N content is at the level of 4E21 atoms/cc. Sharp interfaces between the oxide layers and nitride layers are shown in the N concentration profile.

Example 10: Silicon Nitride Film Depositions on 300 mm Wafers Using Trisilylamine (TSA)

Depositions of silicon nitride films on 300 millimeter (mm) silicon wafers using TSA were performed using an Applied Materials Producer SE system in a 300 mm DXZ chamber fitted with an Astron EM remote plasma generator. The PECVD chamber was equipped with direct liquid injection delivery capability. Thickness and refractive index (RI) at 632 nm were measured by a reflectometer and ellipsometer. Typical film thickness ranged from 100 to 1000 nm. All density measurements were accomplished using X-ray reflectivity (XRR). X-ray Photoelectron Spectroscopy (XPS) and Secondary ion mass spectrometry (SIMS) analysis were performed to determine the elemental composition of the films. The preferred deposition conditions of silicon nitride films using TSA were as follows: TSA flow (500~700 mg/min), NH$_3$ flow (4000~5000 sccm), He (4000~5000 sccm), Pressure (4~8 torr), RF (1000~1200 W), and Temp (40~500° C.).

TABLE 11

| Power (W) | Spacing (mils) | Pressure (Torr) | TSA (mg/min) | He (sccm) | NH$_3$ (sccm) | Deposition Temperature (° C.) |
|---|---|---|---|---|---|---|
| 1200 | 500 | 6 | 675 | 4500 | 5000 | 480 |

The deposition rate was as high as 360 nm/min. The as-deposited films exhibited slightly tensile stress: 0~40 MPa. With the high film density (>2.5 g/cm$^3$), the film shrinkage was ~0.9% after 1 hour annealing at 800° C. The stress change was in the range of 200~250 MPa.

The invention claimed is:

1. A method for depositing a plurality of silicon-containing layers comprising a silicon oxide layer and a silicon nitride layer on at least one surface of a substrate, the method comprising:

providing the at least one surface of the substrate in a reaction chamber;

introducing into the reaction chamber a silicon precursor having the structure of Formula II:

introducing into the reaction chamber a source selected from an oxygen-containing source and a nitrogen-containing source; and depositing via a vapor deposition process the multilayer stack on the at least one surface of the substrate wherein the vapor deposition process is selected from a group consisting of chemical vapor deposition (CVD), plasma enhanced chemical vapor deposition (PECVD), cyclic chemical vapor deposition (CCVD), plasma enhanced cyclic chemical vapor deposition (PECCVD), atomic layer deposition (ALD), and plasma enhanced atomic layer deposition (PEALD); preferably plasma enhanced chemical vapor deposition (PECVD);

wherein the at least one silicon oxide layer comprises one or more of the following properties selected from a density of about 1.9 grams per cubic centimeter (g/cm$^3$ or g/cc) or greater; a hydrogen content of 4×10$^{22}$ atoms/cm$^3$ or less; a stress ranging from about −300 MPa to −100 MPa, a dielectric constant of 4.5 or lower, a leakage current of 10$^{-9}$ A/cm$^2$ or lower at a film breakdown field of 8 MV/cm or higher; and combinations thereof; and wherein the at least one silicon nitride layer described herein comprises one or more of the following properties: a density of about 2.2 g/cm$^3$ or greater; a hydrogen content of about 4×10²² atoms/cm³ or lower, a stress ranging from about 50 MPa to about 300 MPa; a stress change of 300 MPa or less after at least one thermal treatment ranging from about 700 to about 1,000° C., a wet etch rate of 10 nm/min or greater in hot H₃PO₄, and combinations thereof.

2. The method of claim 1 wherein the silicon oxide layer comprises at least one or more of the following properties: a density of about 2.2/cm³ or greater, a stress ranging from about −300 to about −100 MPa, a stress shift of 50 MPa or less after up to 800° C. thermal treatment, and combinations thereof.

3. The method of claim 1 wherein the silicon nitride layer comprises at least one or more of the following properties: a density of about 2.3 g/cm³ or greater, a stress ranging from about 50 to about 300 MPa, a stress shift of 300 MPa or less after up to 800° C. thermal treatment, and combinations thereof.

4. The method of claim 1 wherein the silicon oxide layer has a deposition rate ranging from about 50 nm/min to about 500 nm/min.

5. The method of claim 1 wherein the oxygen-containing source is selected from the group consisting of water (H₂O), oxygen (O₂), oxygen plasma, ozone (O₃), NO, N₂O, carbon monoxide (CO), carbon dioxide (CO₂), N₂O plasma, carbon monoxide (CO) plasma, carbon dioxide (CO₂) plasma, and combinations thereof.

6. The method of claim 1 wherein the nitrogen-containing source is selected from the group consisting of ammonia, hydrazine, monoalkylhydrazine, dialkylhydrazine, nitrogen, nitrogen plasma, nitrogen/hydrogen, nitrogen/helium, nitrogen/argon plasma, ammonia plasma, ammonia/helium plasma, ammonia/argon plasma, ammonia/nitrogen plasma, NF₃, NF₃ plasma, and mixtures thereof.

7. The method of claim 1 wherein the temperature of the depositing step ranges from about 425° C. to about 600° C.

8. The method of claim 1 wherein the deposition process is plasma enhanced chemical vapor deposition (PECVD) or PECCVD.

9. The method of claim 1 wherein the silicon precursor comprises trisilylamine.

10. The method of claim 1 wherein the silicon-containing layer is subjected to a thermal annealing at temperature up to 1000° C.

11. The method of claim 1 wherein the silicon oxide layer comprises substantially zero shrinkage or a shrinkage of about 3% or less or 2% or less or 1% or less and about 50 MPa stress change after thermal treatment up to 800° C.

12. The method of claim 1 wherein the silicon oxide layer comprises substantially zero wet etch rate in hot H₃PO₄.

13. The method of claim 1 wherein the silicon nitride layer comprises a growth rate of 50 nm/min or higher.

14. The method of claim 1 wherein the silicon nitride layer comprises a minimal shrinkage and less than 300 MPa stress change after thermal treatment up to 800° C.

15. The method of claim 1 wherein the number of stacked silicon-containing films comprises alternating silicon oxide and silicon nitride wherein the number of layer of silicon oxide layers ranges from about 48 to about 128 layers and the number of silicon nitride layers is from about 48 to about 128 layers; each silicon oxide layer has identical thickness and each silicon nitride layer has identical thickness.

16. A method for forming an apparatus comprising a plurality of silicon-containing layers wherein the silicon-containing layers are selected from a silicon oxide layer and a silicon nitride layer on at least a surface of a semiconductor substrate, the method comprising:

providing the at least one surface of a semiconductor substrate;

introducing into the reaction chamber a silicon precursor having the structure of Formula II:

(II)

introducing into the reaction chamber a nitrogen-containing source;

depositing via a vapor deposition process the silicon nitride layer;

introducing at least one silicon-containing precursor selected from the group consisting of silane, disilane, tetraethoxysilane (TEOS), triethoxysilane (TES), tetramethoxysilane, trimethoxysilane, di-tert-butoxysilane (DTBOS), di-tert-pentoxysilane (DTPOS), diethylsilane, triethylsilane, diethoxymethylsilane, dimethoxymethylsilane, di(tertiary)butoxymethylsilane, methyltriacetatoxysilane, dimethylacetatoxysilane, dimethyldiacetoxysilane, dimethyldimethoxysilane, dimethyldiethoxysilane, methyltriethoxysilane, neohexyltriethoxysilane, neopentyltrimethoxysilane, diacetoxymethylsilane, phenyldimethoxysilane, phenyldiethoxysilane, phenyltriethoxysilane, phenyltrimethoxysilane, phenylmethyldimethoxysilane, 1,3,5,7-tetramethyltetracyclosiloxane, octamethyltetracyclosiloxane, 1,1,3,3-tetramethyldisiloxane, 1-neohexyl-1,3,5,7-tetramethylcyclotetrasiloxane, hexamethyldisiloxane, 1,3-dimethyl-1-acetoxy-3-ethoxydislioxane, 1,2-diemthyl-1,2-diacetoxy-1,2-diethoxydisilane, 1,3-dimethyl-1,3-diethoxydisiloxane, 1,3-dimethyl-1,3-diacetoxydisilxane, 1,2-dimethyl,1,1,2,2-tetraacetoxydisilane, 1,2-dimethyl-1,1,2,2-tetraethoxydisilane, 1,3-dimethyl-1-acetoxy-3-ethoxydisiloxane, 1,2-dimethyl-1-acetoxy-2-ethoxydisilane, methylacetoxy(tertiary)butoxysilane, methylsilane, dimethylsilane, trimethylsilane, tetramethylsilane, hexamethyldisilane, tetramethyldisilane, and dimethyldisilane, hexamethyldisiloxane (HMDSO), octamethylcyclotetrasiloxane (OMCTS) and tetramethylcyclotetrasiloxane (TMCTS)), bis(triethoxysilyl)methane, bis(triethoxysilyl)ethane, bis(trimethoxysilyl)methane, bis(trimethoxysilyl)ethane, bis(diethoxymethylsilyl)methane, bis(diethoxymethylsilyl)ethane, bis(methyldiethoxysilyl)methane, (diethoxymethylsilyl)(diethoxysilyl)methane and combinations thereof;

introducing into the reaction chamber an oxygen-containing source; and depositing via a vapor deposition process the silicon oxide layer.

17. The method of claim 16 wherein the silicon oxide comprises at least one or more of the following properties: a density of about 2.2/cm³ or greater, a stress ranging from about −300 to about −100 MPa, a stress shift of 50 MPa or less after up to 800° C. thermal treatment, and combinations thereof.

18. The method of claim 16 wherein the silicon nitride comprises at least one or more of the following properties: a density of about 2.3 g/cm³ or greater, a stress ranging from about 50 to about 300 MPa, a stress shift of 300 MPa or less after up to 800° C. thermal treatment, and combinations thereof.

19. The method of claim 16 wherein the silicon oxide layer has a deposition rate ranging from about 50 nm/min to about 500 nm/min.

20. The method of claim 16 wherein the oxygen-containing source is selected from the group consisting of water ($H_2O$), oxygen ($O_2$), oxygen plasma, ozone ($O_3$), NO, $N_2O$, carbon monoxide (CO), carbon dioxide ($CO_2$), $N_2O$ plasma, carbon monoxide (CO) plasma, carbon dioxide ($CO_2$) plasma, and combinations thereof.

21. The method of claim 16 wherein the nitrogen-containing source is selected from the group consisting of ammonia, hydrazine, monoalkylhydrazine, dialkylhydrazine, nitrogen, nitrogen plasma, nitrogen/hydrogen, nitrogen/helium, nitrogen/argon plasma, ammonia plasma, ammonia/helium plasma, ammonia/argon plasma, ammonia/nitrogen plasma, $NF_3$, $NF_3$ plasma, and mixtures thereof.

22. The method of claim 16 wherein the temperature of the depositing step ranges from about 425° C. to about 600° C.

23. The method of claim 16 wherein the deposition process is plasma enhanced chemical vapor deposition (PECVD) or PECCVD.

24. The method of claim 16 wherein the silicon precursor comprises trisilylamine.

25. The method of claim 16 wherein the silicon-containing layer is subjected to a thermal annealing at temperature up to 1000° C.

26. The method of claim 16 wherein the silicon oxide layer comprises substantially zero shrinkage or a shrinkage of about 3% or less or 2% or less or 1% or less and about 50 MPa stress change after thermal treatment up to 800° C.

27. The method of claim 16 wherein the silicon oxide layer comprises substantially zero wet etch rate in hot $H_3PO_4$.

28. The method of claim 16 wherein the silicon nitride layer comprises a growth rate of 50 nm/min or higher.

29. The method of claim 16 wherein the silicon nitride layer comprises a minimal shrinkage and less than 300 MPa stress change after thermal treatment up to 800° C.

30. The method of claim 16 wherein the number of stacked silicon-containing films comprises alternating silicon oxide and silicon nitride wherein the number of layer of silicon oxide layers ranges from about 48 to about 128 layers and the number of silicon nitride layers is from about 48 to about 128 layers; each silicon oxide layer has identical thickness and each silicon nitride layer has identical thickness.

31. A composition for a depositing a plurality of silicon-containing films comprising a silicon-containing precursor having the structure of Formula II (II)

wherein the silicon-containing precursor is substantially free of one or more impurities selected from the group consisting of a halide.

32. The composition of claim 31 wherein the composition further comprises at least one member selected from the group consisting of an oxygen containing source and a nitrogen containing source.

33. A method for forming a plurality of silicon-containing layers wherein the silicon-containing layers are selected from a silicon oxide layer and a silicon nitride layer on at least a surface of a semi-conductor substrate, the method comprising:
providing the at least one surface of a semiconductor substrate;
introducing a silicon-containing precursor having the structure of Formula II:

(II)

introducing into the reaction chamber a nitrogen-containing source;
depositing via a vapor deposition process the silicon nitride layer;
introducing a silicon-containing precursor having the structure of Formula II:

(II)

introducing into the reaction chamber an oxygen-containing source; and
depositing via a vapor deposition process the silicon oxide layer; wherein the method is repeated to provide a multilayer stock of alternating silicon nitride and silicon oxide layers.

34. A method for forming a plurality of silicon-containing layers wherein the silicon-containing layers are selected from a silicon oxide layer and a silicon nitride layer on at least a surface of a semi-conductor substrate, the method comprising:
providing the at least one surface of a semiconductor substrate;
introducing a silicon-containing precursor having the structure of Formula II:

(II)

introducing into the reaction chamber a nitrogen-containing source;
depositing via a vapor deposition process the silicon nitride layer;
introducing at least one silicon-containing precursor comprising tetraethyl orthosilicate;
introducing into the reaction chamber an oxygen-containing source; and
depositing via a vapor deposition process the silicon oxide layer; wherein the method is repeated to provide a multilayer stock of alternating silicon nitride and silicon oxide layers.

* * * * *